(12) United States Patent
Hsieh et al.

(10) Patent No.: US 7,570,733 B2
(45) Date of Patent: Aug. 4, 2009

(54) STEP-AND-SHOOT CARDIAC CT IMAGING

(75) Inventors: Jiang Hsieh, Brookfield, WI (US);
Jianying Li, New Berlin, WI (US);
Xiangyang Tang, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 261 days.

(21) Appl. No.: 11/149,993

(22) Filed: Jun. 10, 2005

(65) Prior Publication Data

US 2006/0280283 A1 Dec. 14, 2006

(51) Int. Cl.
*A61B 6/00* (2006.01)

(52) U.S. Cl. ............................................. 378/8; 378/4

(58) Field of Classification Search .................... 378/8, 378/4–20, 15, 19, 65, 95, 901
See application file for complete search history.

(56) References Cited

U.S. PATENT DOCUMENTS

| | | | | |
|---|---|---|---|---|
| 4,182,311 A * | 1/1980 | Seppi et al. | ................ | 600/428 |
| 4,339,799 A * | 7/1982 | Abele et al. | ................ | 378/11 |
| 4,903,704 A * | 2/1990 | Van Eggermond et al. | .. | 600/413 |
| 5,216,601 A * | 6/1993 | Crawford et al. | ............. | 378/14 |
| 5,233,518 A * | 8/1993 | King et al. | ................... | 378/14 |
| 5,295,488 A * | 3/1994 | Lloyd et al. | ................ | 600/410 |
| 5,960,056 A * | 9/1999 | Lai | ............... | 378/4 |
| 5,991,356 A * | 11/1999 | Horiuchi et al. | ............... | 378/8 |
| 6,061,423 A * | 5/2000 | Hsieh | ................... | 378/15 |
| 6,154,516 A * | 11/2000 | Heuscher et al. | ............. | 378/15 |
| 6,243,437 B1 * | 6/2001 | Hu et al. | ................... | 378/8 |
| 6,275,560 B1 * | 8/2001 | Blake et al. | ................... | 378/8 |
| 6,307,910 B1 * | 10/2001 | Acharya et al. | ............... | 378/4 |
| 6,324,247 B1 * | 11/2001 | Besson | ................... | 378/15 |
| 6,324,254 B1 * | 11/2001 | Pflaum | ................... | 378/95 |
| 6,370,217 B1 * | 4/2002 | Hu et al. | ................ | 378/8 |
| 6,393,091 B1 * | 5/2002 | Slack et al. | ................... | 378/8 |
| 6,408,043 B1 * | 6/2002 | Hu et al. | ................ | 378/8 |
| 6,421,552 B1 * | 7/2002 | Hsieh | ................... | 600/425 |
| 6,466,640 B1 * | 10/2002 | Taguchi | ................... | 378/15 |
| 6,470,066 B2 * | 10/2002 | Takagi et al. | .................. | 378/8 |
| 6,480,560 B2 * | 11/2002 | Hsieh | ................... | 378/8 |
| 6,490,333 B1 * | 12/2002 | Hsieh | ................... | 378/4 |
| 6,522,712 B1 * | 2/2003 | Yavuz et al. | ................... | 378/4 |
| 6,529,576 B2 * | 3/2003 | Hsieh et al. | ................... | 378/15 |
| 6,639,965 B1 * | 10/2003 | Hsieh et al. | ................... | 378/8 |
| 6,721,386 B2 | 4/2004 | Bulkes et al. | .................. | 378/8 |
| 6,836,529 B2 | 12/2004 | Li et al. | ................... | 378/8 |
| 7,006,593 B2 * | 2/2006 | Kokubun et al. | ............... | 378/8 |
| 7,058,440 B2 * | 6/2006 | Heuscher et al. | ............. | 600/428 |
| 7,177,386 B2 * | 2/2007 | Mostafavi et al. | .............. | 378/4 |
| 2002/0118790 A1 * | 8/2002 | Pan et al. | ................... | 378/8 |
| 2002/0136350 A1 * | 9/2002 | Pan et al. | ................... | 378/8 |

(Continued)

*Primary Examiner*—Edward J Glick
*Assistant Examiner*—Alexander H Taningco
(74) *Attorney, Agent, or Firm*—Ziolkowski Patent Solutions Group, SC

(57) ABSTRACT

The present invention is directed to a method and system of blending data acquired from neighboring partial-scans. Data is acquired from an imaging volume in a series of fractional or partial-scans. Each partial-scan samples a fraction of the imaging volume. During reconstruction, data from the partial-scans are combined to compensate for the unsampled portion of the imaging volume that is experienced in any partial-scan alone.

24 Claims, 7 Drawing Sheets

U.S. PATENT DOCUMENTS

| | | | |
|---|---|---|---|
| 2002/0141531 A1* | 10/2002 | Taguchi | 378/19 |
| 2004/0017881 A1* | 1/2004 | Cesmeli et al. | 378/4 |
| 2004/0077941 A1* | 4/2004 | Reddy et al. | 600/428 |
| 2004/0081269 A1* | 4/2004 | Pan et al. | 378/4 |
| 2005/0089133 A1* | 4/2005 | Tsuyuki | 378/8 |
| 2006/0039537 A1* | 2/2006 | Strobel | 378/197 |
| 2006/0274878 A1* | 12/2006 | Hsieh et al. | 378/8 |

* cited by examiner

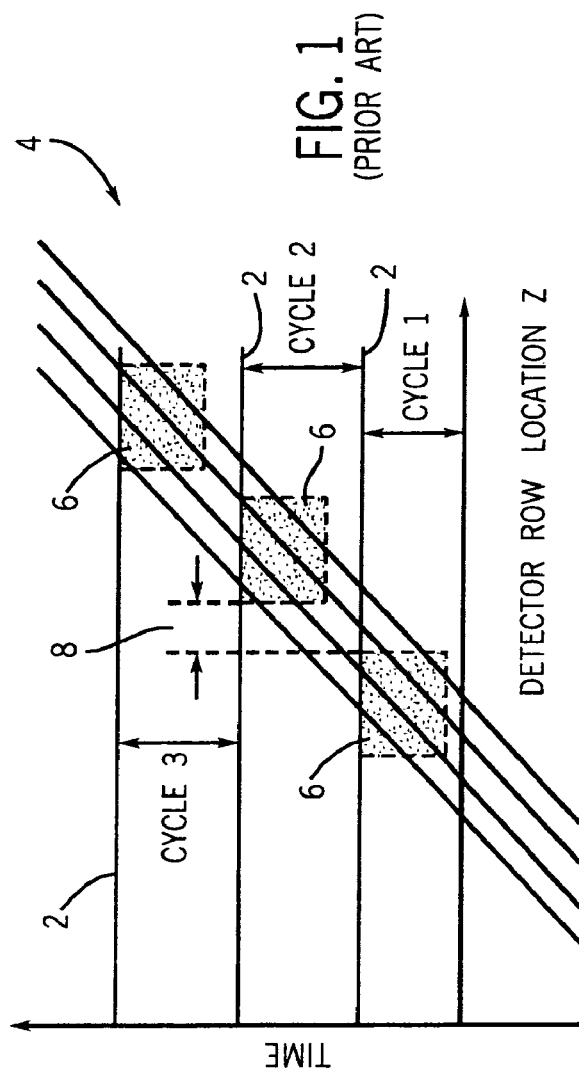
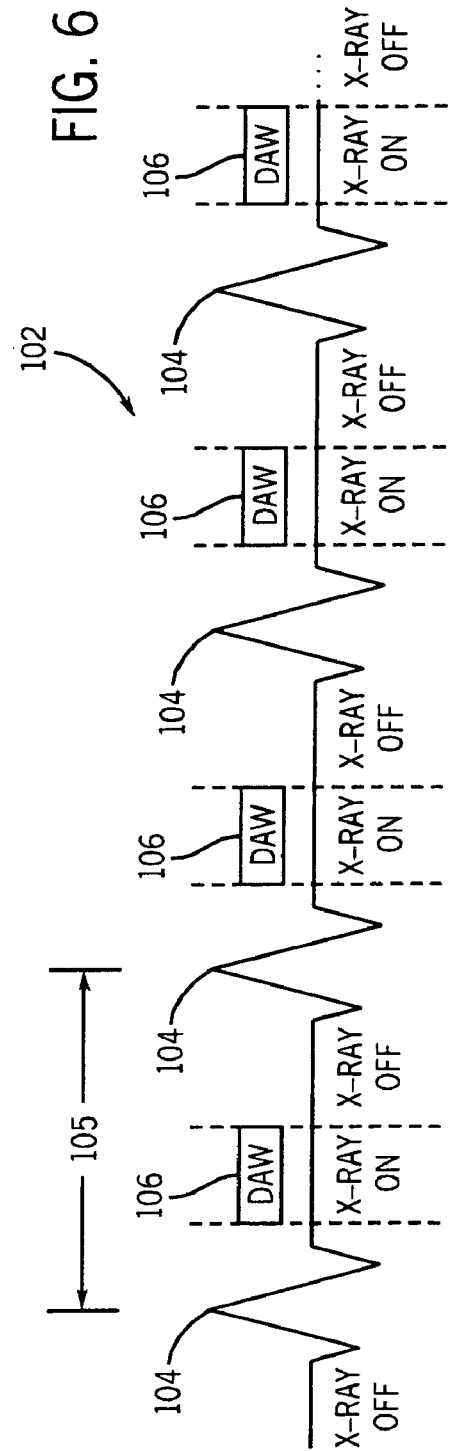

STEP-AND-SHOOT CARDIAC CT IMAGING

BACKGROUND OF THE INVENTION

The present invention relates generally to diagnostic imaging and, more particularly, to a method and apparatus of cardiac CT imaging using a series of partial-scans to sample an imaging volume and image blending during image reconstruction.

The narrowing or constriction of vessels carrying blood to the heart is a well-known cause of heart attacks and, gone untreated, can lead to sudden death. In such stenotic vessels, it is known that the region immediately downstream from the constriction is characterized by having rapid flow velocities and/or complex flow patterns. In general, narrowing of blood carrying vessels supplying an organ will ultimately lead to compromised function of the organ in question, at best, and organ failure, at worst. Quantitative flow data can readily aid in the diagnosis and management of patients and also help in the basic understanding of disease processes. There are many techniques available for the measurement of blood flow, including imaging based methods using radiographic imaging of contrast agents, both in projection and computed tomography (CT), ultrasound, and nuclear medicine techniques. Radiographic and nuclear medicine techniques often require the use of ionizing radiation and/or contrast agents. Some methods involve making assumptions about the flow characteristics which may not necessarily be true in vivo or require knowledge about the cross-sectional area of the vessel or the flow direction.

CT is one technique of acquiring blood flow and other cardiac data. Typically, in CT imaging systems, an x-ray source emits a fan-shaped beam or cone-shaped beam toward a subject or object. Hereinafter, reference to a "subject" shall include anything capable of being imaged. The beam, after being attenuated by the subject, impinges upon an array of radiation detectors. The intensity of the attenuated beam of radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image. Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

Increasingly, CT imaging is being used for cardiac imaging. This increase in the implementation of CT for cardiac imaging is primarily predicated upon the relatively fast scan speeds that are now possible with CT systems and the acquisition of multi-slice data. Conventional CT systems are now capable of supporting 0.35 seconds per gantry rotation, if not faster. In fact, in the past decade, there has been nearly a three-fold improvement in temporal resolution. Multi-slice CT acquisition has also contributed to the rise of cardiac CT imaging for cardiac-related diagnoses. CT systems are now capable of significant multi-slice acquisitions.

One application of cardiac CT imaging is coronary artery imaging (CAI). The objective of CAI is to capture images and thus visualize the vasculature of the heart to detect vascular narrowing, disease, or anomalies. CAI is often used by cardiologists, radiologists, and other physicians to examine the dynamic motion of the heart muscles to detect abnormalities. To visualize the narrowing or constriction of a small vessel, the CT scan must provide high temporal resolution so as to "freeze" the cardiac motion in and around the vessel as well as provide high spatial resolution to accurately depict the size of the vessel under examination.

To improve temporal resolution, CAI studies are typically carried out with the assistance of electrocardiogram (ECG) signals acquired from the patient using an ECG monitor. An ECG monitor records the electrical activity of the heart using electrodes placed on the patient's chest, arms, and legs. An ECG monitor is commonly used to provide information regarding heart rate, heart rhythm, adequacy of blood supply to the heart, presence of a heart attack, enlargement of the heart, pericarditis, and the effects of drugs and electrolytes on the heart. ECG signals may also be used to provide cardiac phase data so as to synchronize the acquisition of CT data from the heart with the phase activity of the heart. More particular, the CT system uses the ECG signals to consistently acquire data during the same phase of the cardiac cycle during the CT scan. Doing so reduces image artifacts.

In conventional helical CAI scans, the table translates the patient continuously at a relatively slow pace, i.e. low-pitch, to ensure that the entire heart volume is properly covered. This is illustrated in FIG. 1 where detector row position as a function of time is plotted. As shown, the cardiac cycles are separated by horizontal dotted lines 2. The detector-row locations are depicted by the solid diagonal lines 4. Every point on these lines represents a single-row projection collected at a certain z location and a particular time (therefore a particular projection angle). The z-axis extends along the length of the imaging table, as shown in FIG. 2. For simplicity of illustration, a four-row system is illustrated. The shaded boxes 6 show the reconstruction windows for the cardiac images. These boxes 6, therefore, depict a unique set of time intervals and z-locations. The width of each box 6 represents the volume in z that can be covered with reconstructions corresponding to a particular cardiac cycle. The adjacent set of reconstructions take place only after the heart reaches the same cardiac phase in the next cardiac cycle. If the combination of gantry speed and helical pitch is not properly selected, the entire heart volume will not be uniformly covered in the reconstructed images. For example, if the table travels too fast (helical pitch is too high), gaps 8 will be present between adjacent volumes. Although small gaps could be filled by image space interpolation, larger gaps will lead to discontinuities and artifacts in the volume rendered images. This is particularly problematic when considering the variation of heart rate in a typical patient.

Conventional CAI studies are typically carried out with helical pitches between 0.1 and 0.4. Such a helical pitch is commonly used to account for the worst case scenario with regards to timing, i.e. ensure complete volume coverage at specified heart rate for a given reconstruction. This translates to a higher dose to patients since regions exposed to the x-ray radiation are highly overlapped. That is, since for a typical helical scan x-rays are continuously projected toward the subject, these regions of overlap correspond to regions that are exposed to multiple exposures of x-ray radiation. To reduce dose to the patient during CAI studies, a number of dose reduction techniques have been developed. In one technique, the current to the x-ray tube is modulated such that the current is reduced outside the reconstruction window defined between each heartbeat. While these techniques have advantageously reduced dose, cardiac imaging remains to be one of the highest x-ray dose applications in CT.

One proposed solution to reduce x-ray dose during cardiac CT is commonly referred to as "half-scans". With half-scan imaging, data acquisition is segmented into a number of half-scans wherein each half-scan samples approximately one-half of a sampling volume. Typically, however, each half-scan has a spatial coverage that substantially overlaps a neighboring half-scan. As a result, dose is reduced but not significantly so that image fidelity is maintained.

Therefore, it would be desirable to design an apparatus and method for cardiac CT imaging that further reduces x-ray dose as well as improves temporal and spatial resolution of CT images. It would also be desirable to have a method and system to carry out partial-scan acquisitions with reduced overlapping in spatial coverage of neighboring partial-scans to appreciate a reduction in subject dose during data acquisition.

BRIEF DESCRIPTION OF THE INVENTION

The present invention is directed to a method and apparatus for cardiac CT imaging that overcomes the aforementioned drawbacks.

The invention includes an imaging technique whereby a subject is incrementally translated through a number of discrete scan positions for the acquisition of CT data from a cardiac region of the subject. In this regard, the subject is not translated to the next scan position until valid or acceptable data is acquired for a current scan position. As such, the invention takes into account cardiac irregularities such as arrhythmias during the acquisition of data. That is, if an abnormality is detected, the subject is not translated to a next scan position. Rather, data is reacquired at the current scan position during the next cardiac cycle. The invention is also applicable to other physiological gated acquisitions, such as respiratory gated CT imaging.

The invention also includes a reconstruction technique whereby an imaging volume is sampled in a series of partial or fractional scans. Each partial-scan samples less than all of the imaging volume. During reconstruction, data from neighboring partial-scans is used to compensate for the unsampled portion of the image volume that occurs in any partial-scan alone.

Therefore, in accordance with one aspect, a CT scanner is disclosed and includes an x-ray source configured to project x-rays at a subject to be scanned and an x-ray detector assembly configured to detect x-rays projected by the x-ray source and attenuated by the subject. The CT scanner also includes a computer programmed to define an imaging volume to be imaged in a pair of neighboring partial-scans and cause acquisition of a first set of CT data from less than all the imaging volume in a first partial-scan. The computer is further programmed to cause acquisition of a second set of CT data from less than all the imaging volume in a second partial-scan and combine the first and the second sets of CT data into a composite dataset having a spatial coverage of the imaging volume. The computer then reconstructs a CT image of the imaging volume from the composite dataset.

In accordance with another aspect of the present invention, a method of CT imaging includes the steps of defining an imaging volume from which CT data is to be acquired and translating a subject to be scanned to one of a number of discrete scan positions. The method further includes repeatedly acquiring CT data from the imaging volume in a series of fractional scans while the subject is positioned at the one discrete scan position and blending the CT data acquired with the series of fractional scans into a single dataset for reconstruction.

According to another aspect, the invention includes a computer readable storage medium having a computer program stored thereon and representing a set of instructions that when executed by a computer causes the computer to acquire a first set of cardiac gated CT data in a first half-scan and acquire a second set of cardiac gated CT data in a second half-scan that captures the second set of cardiac gated CT data from a portion of a sampling region that neighbors another portion of the sampling region from which the first set of cardiac gated CT data is acquired. The computer is further caused to compare the first set of cardiac gated CT data to the second set of cardiac gated CT data to determine a weighting function and weight the first set of cardiac gated CT data by the weighting function. The computer then combines the weighted first set of cardiac gated CT data with the second set of cardiac gated CT data for image reconstruction of the sampling region.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 1 is a plot of time versus detector row location in z illustrating the coverage gap that is possible with a conventional cardiac CT acquisition.

FIG. 6 is a schematic of an exemplary ECG signal.

DETAILED DESCRIPTION OF THE PREFERRED EMBODIMENT

Figure 2:
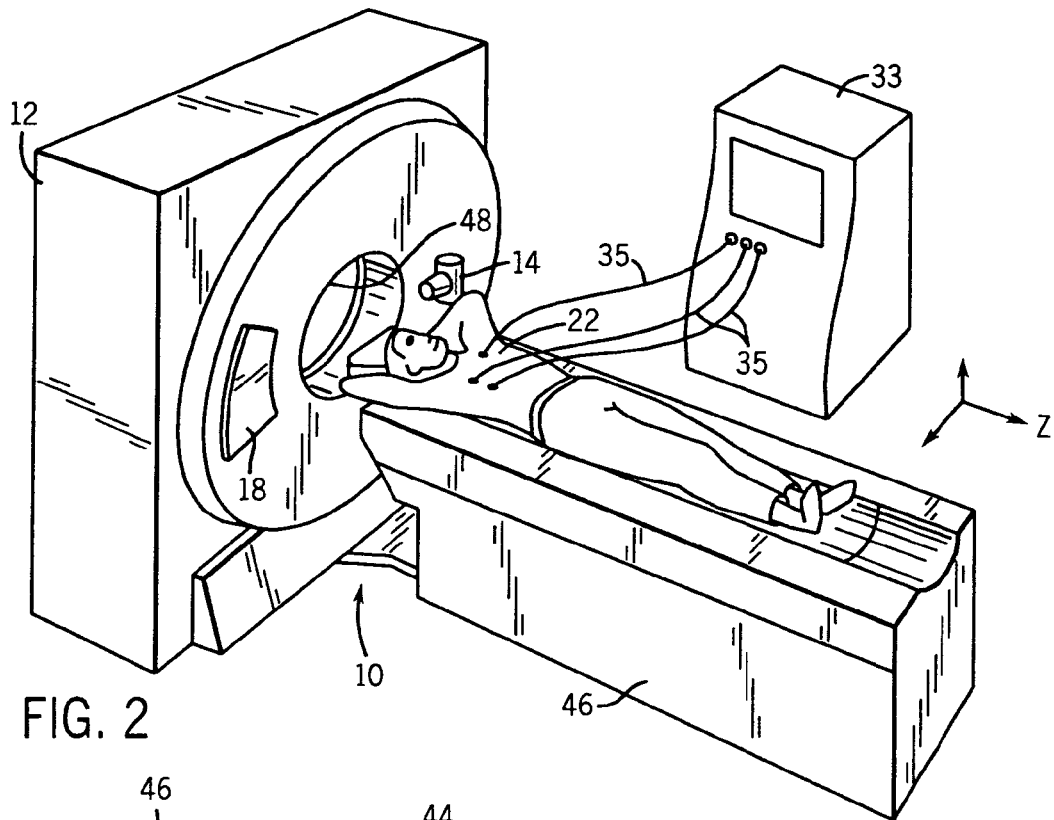
FIG. 2 is a perspective view of a CT system incorporating the present invention.
Figure 3:
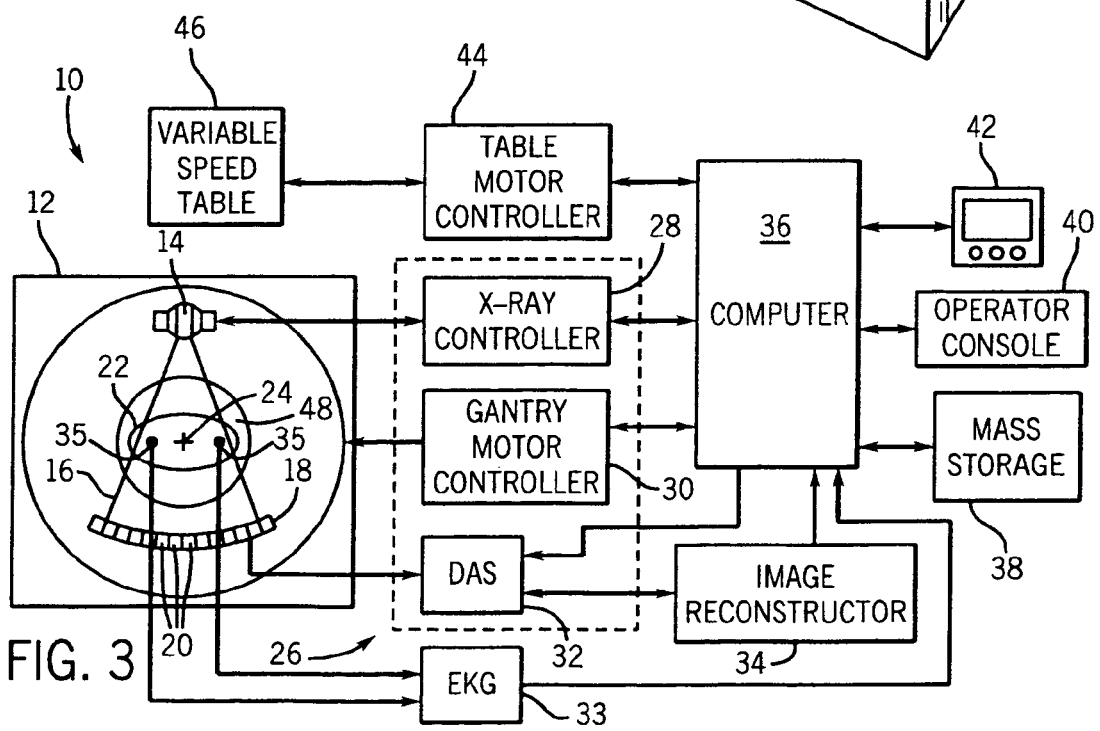
FIG. 3 is a block schematic diagram of the system illustrated in FIG. 2.

Referring to FIGS. 2 and 3, a computed tomography (CT) imaging system 10 is shown as including a gantry 12 having an x-ray source 14 that projects a beam of x-rays 16 toward a detector array 18 on the opposite side of the gantry 12. Detector array 18 is formed by a plurality of detectors 20 that together sense the projected x-rays that pass through a medical patient 22. In a preferred embodiment, detector array 18 has 64 rows of detectors for the acquisition of 64 slices of data in a single gantry rotation. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. As will be described below, computer 36 also receives ECG signals from an ECG 33 connected to the subject via leads 35 to acquire cardiac data of the subject 22. The computer 36 correlates the ECG signals to determine the phases of the cardiac region. Preferably, the ECG machine 33 obtains an ECG recording of the patient before scanning commences such that data acquisition can be timed to occur during quiescent periods between peaks of a cardiac cycle. During these quiescent periods, the heart is relatively still and, therefore, it is preferred for data acquisition to occur during these portions of the cardiac cycle to minimize motion artifacts in the final reconstructed image. An image reconstructor 34 receives sampled and digitized x-ray data from DAS 32 and performs high-speed reconstruction. The reconstructed image is applied as an input to a computer 36 that stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, ECG monitor 33, and gantry motor controller 30. In addition, computer 36 operates a table motor controller 44 that controls a motorized table 46 to position patient 22 and gantry 12. Particularly, table 46 moves portions of patient 22 through a gantry opening 48.

The present invention is directed to a technique of cardiac CT imaging applicable with the system illustrated in FIGS. 2-3, or equivalents thereof.

In conventional cardiac CT imaging, a helical scan is used. Helical scans are commonly employed because they advantageously eliminate an inter-scan delay. That is, with a helical scan, x-ray projection toward the subject is continuous as is table translation through the opening in the gantry. As a result, helical scans are generally not well-suited for physiological gated scans, such as cardiac imaging, as a result of the lack of flexibility to independently select acquisition location and timing. In helical scans, the table is translated or indexed at a constant speed. This has been shown to be problematic for patients that experience a variation in heart rate during data acquisition.

Figure 4:
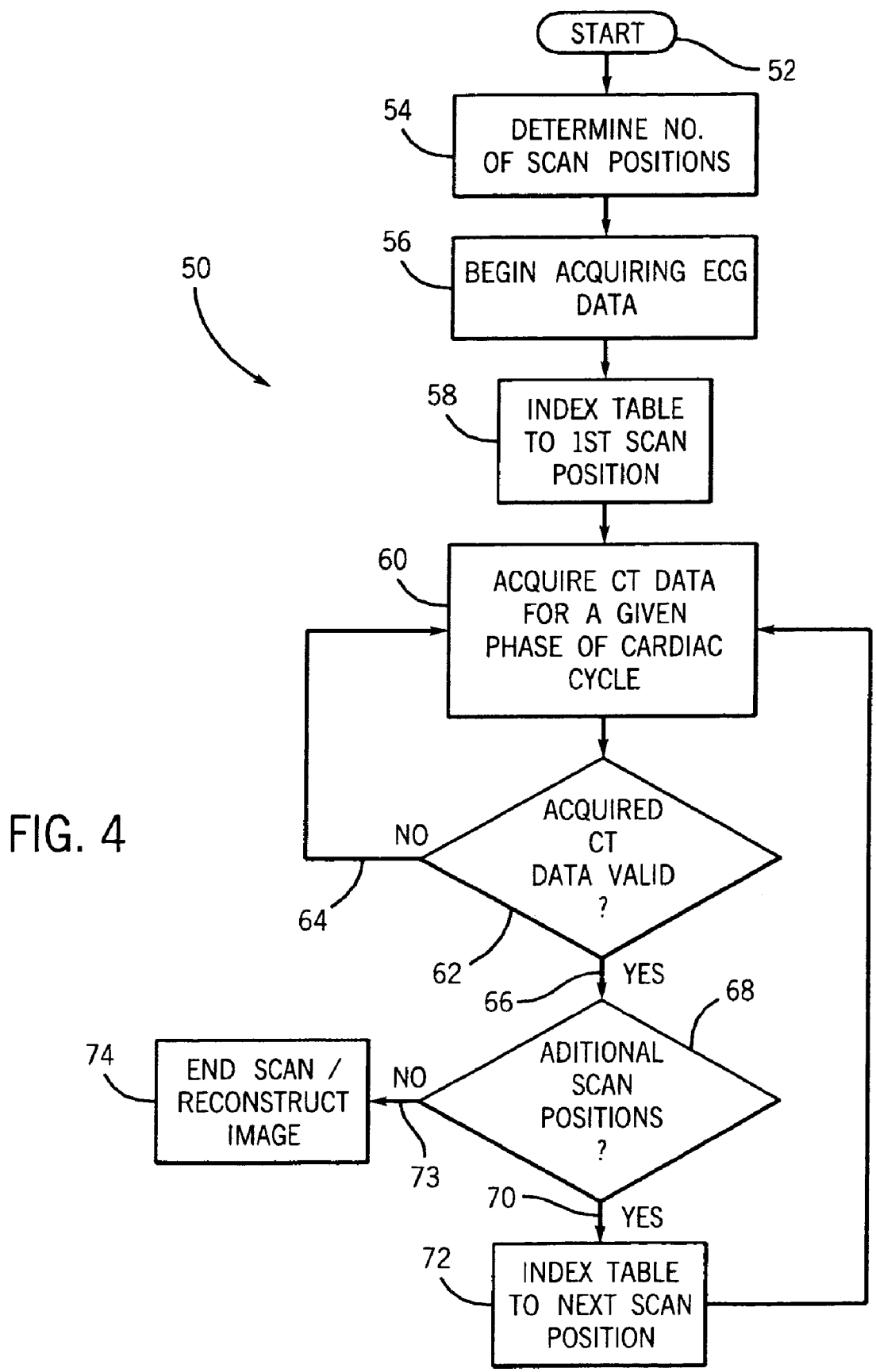
FIG. 4 is a flow chart setting forth the steps of a cardiac CT data acquisition in accordance with the present invention.

Referring now to FIG. 4, a technique 50 to incrementally step a subject through a number of discrete scan positions in accordance with one embodiment of the present invention will be described. The technique will be described with respect to cardiac imaging, but is applicable with other physiologically gated acquisitions. One skilled in the art will appreciate that the technique illustrated in FIG. 4 may be embodied in the set of instructions of a computer program that may be executed by one or more processors of the CT system. Additionally, the computer program may be stored on a computer readable storage medium, such as a CD, or embodied in a computer data signal that is downloadable to a CT system.

Technique 50 begins at 52 with the prescription of a cardiac CT scan. In this regard, electrodes of an ECG monitor are attached to the subject and the subject is properly positioned on the table that is designed to move the subject fore and aft through the opening defined within the gantry. Based on the prescription identified at 52, a number of discrete scan positions is determined at 54. For example, for a CAI study, the number of discrete scan positions would be typically four or five positions for 40 mm detector coverage. That is, the entire volume of the heart of a subject can, typically, be scanned in four or five scan positions. ECG data is continuously acquired throughout the acquisition starting at 56 from the subject. As described above, the computer of the CT system then correlates the ECG signals to determine the phases of the subject's heart motion. In this regard, it is preferred that reading and analysis of the ECG recordings of the subject begins before scanning commences so that data acquisition can be timed to occur between peaks of a cardiac cycle. During these relatively quiet periods, the heart is still and it is, therefore, preferred for data acquisition to occur during these portions of the cardiac cycle to minimize motion artifacts. Thereafter, the table having the scan subject disposed thereon is indexed to the first scan position 58. Thereat, CT data is acquired for a given phase of the cardiac cycle 60.

Once data is acquired for the given phase of cardiac cycle with the subject positioned at the first scan position, a determination is made as to whether the acquired CT data is valid 62. If valid data is not acquired 62, 64, technique 50 returns to step 60 with the reacquisition of data for the given phase of the cardiac cycle with the subject still positioned at the first scan position. However, if valid CT data is acquired 62, 66, then technique 50 proceeds to step 68 and determines if additional scan positions remain 68. If so 68, 70, the table is indexed to the next scan position 72 whereupon data is acquired for the given phase of cardiac cycle with the subject positioned at the next scan position.

However, if data has been acquired for all scan positions 68, 73, the scan ends at 74 with reconstruction of an image.

Technique 50, as described above, is directed to the acquisition of gated CT data from a cardiac region of a subject whereby the subject is incrementally translated through a number of scan positions for the acquisition of data. In contrast to conventional gated acquisitions, table motion is discontinuous. That is, the subject is positioned at a discrete scan position, data is acquired from the subject, a determination is made to determine if the data acquired is valid, and, if so, the subject is translated to the next discrete scan position. If the acquired data is invalid, then the subject remains fixed at the current scan position and data is reacquired. In this regard, the subject does not proceed to the next scan position until valid data is acquired for the current scan position.

Additionally, in a preferred embodiment, x-ray projection toward the subject only occurs during data acquisition. That is, during the intervals in which the table is moved from one scan position to the next scan position, it is preferred that x-ray projection be disabled. In this regard, as data is not acquired during translation of the table, x-ray exposure to the subject does not occur during translation of the table. In this regard, technique 50 advantageously further reduces patient exposure to radiation when compared to conventional helical gated acquisitions.

Figure 5:
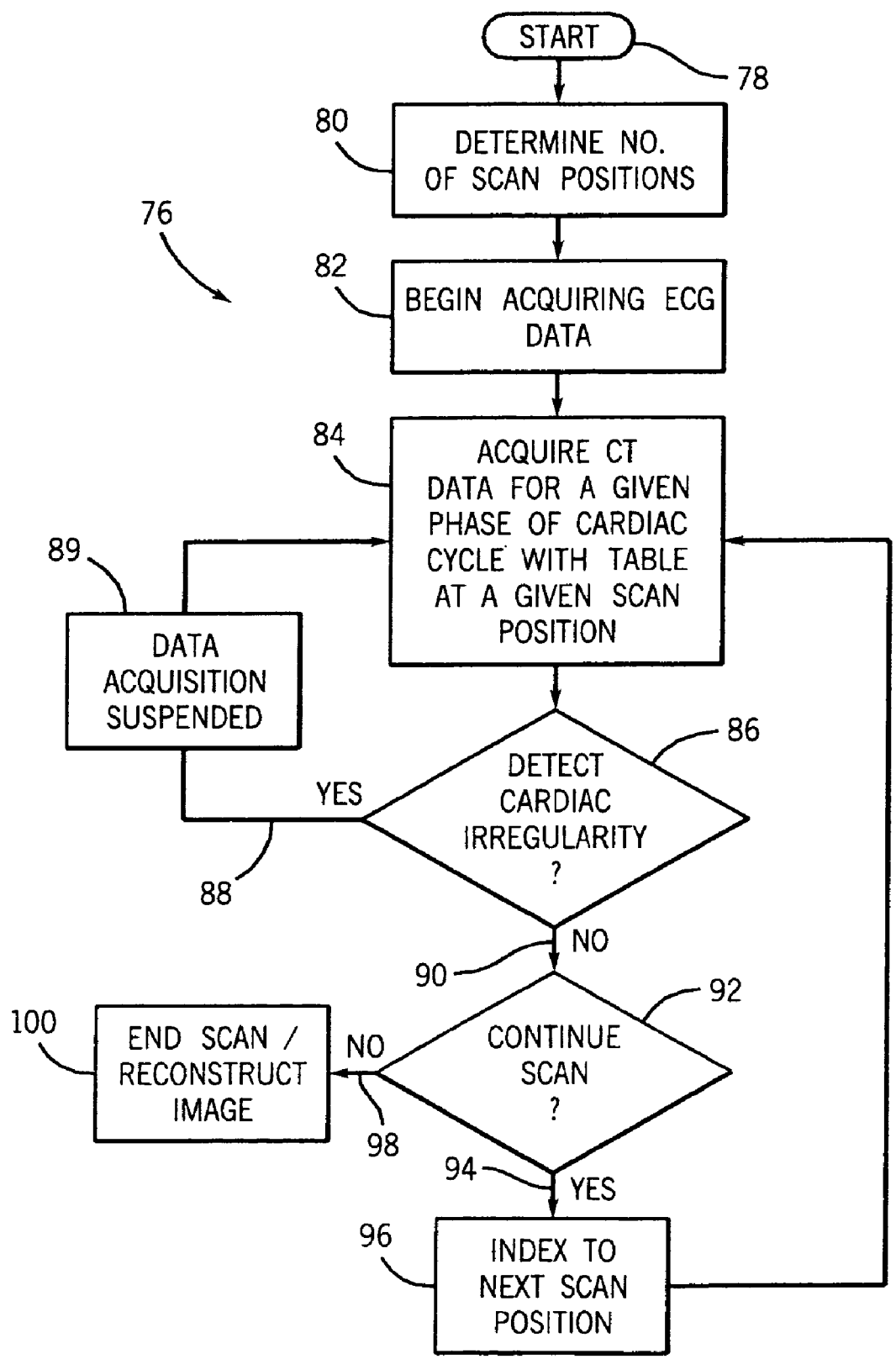
FIG. 5 is a flow chart setting forth the steps of a cardiac CT data acquisition in accordance with another embodiment of the present invention.

Referring now to FIG. 5, not only is the present invention directed to a technique, such as that described in FIG. 4 that incrementally translates a subject to a number of discrete scan positions, the present invention also includes a technique 76 for interrupting or suspending data acquisition at a given scan position based on a detected irregularity or abnormality in the received ECG signals. While technique 76 will be described independent of the technique described with respect to FIG. 4, one skilled in the art will appreciate that technique 76 may be carried out in conjunction with technique 50 of FIG. 4. Technique 76 begins at step 78 with the prescription of a cardiac CT scan. Thereafter, based on the scan parameters identified at step 78, a number of discrete scan positions is determined at 80. As discussed above, to image the heart of a typical patient, four or five discrete scan positions are needed. Similar to the technique of FIG. 4, ECG data is acquired at 82 prior to the commencement of the CT scan. The acquired ECG data is used by the CT system to correlate the acquisition of CT data from a given phase of the cardiac cycle. One skilled in the art will appreciate, however, that ECG signals are also acquired during the acquisition of CT data. CT data is acquired 84 for a given phase of the cardiac cycle with the subject positioned at a given scan position. While the CT data is being acquired 84, the received ECG signals are monitored to determine if any cardiac irregularities have occurred 86. If so, 86, 88, data acquisition for the given scan position is suspended at 89. In this regard, the acquisition of data for the given phase of the cardiac cycle from the subject will recommence in the next cardiac cycle. If a cardiac irregularity is not detected 86, 90, technique 76 proceeds to step at 92 and determines whether the scan should continue 92, i.e. additional scan positions remain. If so 92, 94, the table is indexed to the next scan position at 96 whereupon data is acquired for the given phase of the cardiac cycle of the subject at the next scan position. Steps 84 through 92 are then re-executed until data has been acquired for all scan positions. Once data has been acquired for all scan positions 92, 98, technique 76 proceeds to step 100 where the scan ends and an image is reconstructed 100.

Referring now to FIG. 6, an exemplary ECG signal 102 is shown. ECG signal 102 graphically illustrates movement of the heart of a subject during a cardiac cycle. As illustrated, the cardiac cycle, i.e., heartbeat, is typically defined by a pair of R-peaks 104. In this regard, a single heartbeat is characterized by an R-R interval 105. As described above, the present invention advantageously reduces x-ray dose to the patient. This is achieved by defining a data acquisition window 106 within each R-R interval 105. As such, x-rays are projected toward the subject only during the data acquisition window 106. In this regard, x-ray emission is disabled during other periods of the R-R interval 105. One skilled in the art will appreciate that the data acquisition window 106 corresponds to the phase of the heart during which data acquisition is to occur. As such, during those phases of the cardiac cycle in which data acquisition is not to occur, the x-ray tube is controlled not to project x-rays toward the subject. Moreover, since data acquisition, timing, and location can be treated independently, gating is more effective. Additionally, even for the case in which all cardiac phases need to be acquired and reconstructed, the acquisition ensures that an overlap of x-ray exposure is not required in the covered regions. That is, all the regions are scanned only once which is in contrast to low-pitch helical acquisitions where the majority of the scan volume is scanned multiple times. Testing has shown that a 67% to 83% reduction in dose can be expected with the present invention when compared to conventional low-pitch helical scans.

Figure 7:
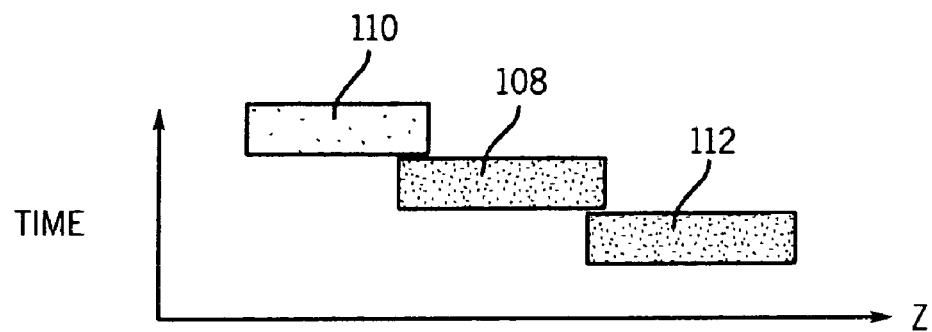
FIG. 7 is a schematic illustrating overlapping data acquisition regions in accordance with another embodiment of the present invention.

Referring now to FIG. 7 and in accordance with another embodiment of the present invention, overlapping data acquisitions are used to reduce artifacts. Data acquisition 108 overlaps partially with data acquisition 110 and data acquisition 112. This overlapping is exploited to address two major challenges in cardiac imaging: inconsistent heart rate and cone beam. That is, in a typical patient, heart rate varies. Even at a relatively constant heart rate 108, 110, 112, heart motion does not exactly replicate cycle to cycle. Since data acquisitions 108, 110, 112 take place in different cardiac cycles, if not addressed, inconsistency between the heart cycles can lead to shifted boundaries. In addition, for cone beam data acquisitions, some cone beam related artifacts can be present in the images. As such, the overlapped region 108 provides a tool to "blend" regions 108-112 together in a more consistent manner. This blending can take place either during the reconstruction or after reconstruction of an image.

Figure 8:
FIG. 8 is a schematic representation of an exemplary ECG signal illustrating data acquisition time and inter-scan delay relative to a given cardiac cycle.

In yet another embodiment and referring to FIG. 8, gantry speed, interscan delay, and coverage are determined based on the patient heart rate, schematically illustrated by ECG signal 114. For the step-and-shoot acquisition described herein, the total scan time is defined by the data acquisition time and the inter-scan delay. The data acquisition time 116 is the time used to collect data and the inter-scan delay 118 is to move the patient or table to the next location and ready the patient for scanning. When the total scan time is less than a patient heart cycle, the next scan can start without any gap in the patient heart cycle. If the total scan time is larger than the heart cycle, scanning cannot start at the next heart cycle. This next heart cycle must be skipped. If the total scan time is larger than two cardiac cycles, two idle cycles will be present in which no data acquisition takes place. By changing the gantry scan speed (changing the data acquisition time) and the amount of distance that the table has to travel (changing the inter-scan delay), the total scan time can be modified so that a minimum time is spent at idle. If it is necessary to reduce the table travel distance, then pre-patient collimation may be changed to reduce x-ray dose to patient. That is, if the largest distance the table can travel to fit within a single cardiac cycle is 35 mm, x-ray coverage must be reduced by collimating down the primary x-ray beam to 35 mm, i.e. from 35 mm to 40 mm, so that additional dose is not applied to patient.

Figure 9:
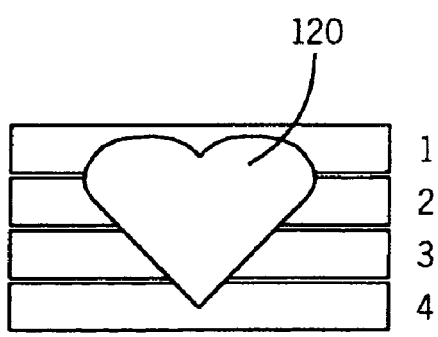
FIG. 9 is a schematic illustrating sequential scanning of a heart in a conventional manner.
Figure 10:
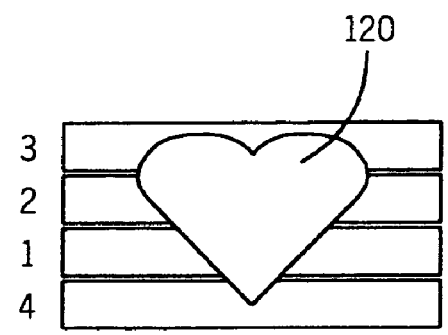
FIG. 10 is a schematic illustrating non-sequential scanning of a heart in accordance with one embodiment of the present invention.

Referring now to FIGS. 9 and 10 of the present invention, in another embodiment, the entire heart can be scanned "out of sequence", to reduce total acquisition time and/or improve image quality. For example, in a conventional acquisition, the heart 120 is covered sequentially from top to bottom, as illustrated in FIG. 9. However, for a given scan, it may be advantageous to start from a middle or top location and skip a location to scan another part for contrast optimization as illustrated in FIG. 10.

Additionally, it is contemplated that different parts of the heart can be scanned in slightly different cardiac phases. It is well known that the entire heart does not move in complete synchrony. As such, the best resting phase for the right atrium may not be the best location for the left ventricle. Accordingly, the present invention allows each location to be acquired independently. As such, modification can be made to tailor the acquisition to the anatomy.

In another embodiment, the present invention is directed to controlling rotational speed of the gantry during data acquisition to maintain a desired relationship between projection angles of neighboring half-scans. Half-scan imaging is a common imaging technique for cardiac CT imaging to improve temporal resolution. With half-scan imaging, projections over the projection angle of $\pi+2\gamma_m$ is used instead of $2\pi$, where $\gamma_m$ is the fan angle of the detector. Such a reconstruction can be characterized by the following equation:

$$f(x, y, z) = \frac{1}{2}\int_0^{\pi+2\gamma_m} \left(\frac{D}{D+y'}\right)^2 d\beta \times \qquad \text{Eqn. (1)}$$

$$\int_{-\infty}^{\infty} \frac{D}{\sqrt{D^2 + s^2 + v^2}}$$

$$w(s, \beta)q(s, v, \beta)h(s' - s)ds$$

where $w(s, \beta)$ is the half-scan weight:

$$w(s,\beta) = 3\theta^2(\gamma,\beta) - 2\theta^3(\gamma,\beta) \qquad \text{Eqn. (2),}$$

and $$\theta(\gamma, \beta) = \begin{cases} \dfrac{\beta}{2\gamma_m - 2\gamma}, & 0 \leq \beta < 2\gamma_m - 2\gamma, \\ 1, & 2\gamma_m - 2\gamma \leq \beta < \pi - 2\gamma, \\ \dfrac{\pi + 2\gamma_m - \beta}{2\gamma_m - 2\gamma}, & \pi - 2\gamma \leq \beta < \pi + 2\gamma_m. \end{cases} \qquad \text{Eqn. (3)}$$

where D is x-ray source to the system isocenter distance, s and v are the projection channel and row locations according to the reconstructed pixel (x,y,z), $\beta$ is the projection angle, and $\gamma$ is the detector fan angle corresponding to s.

Figure 11:
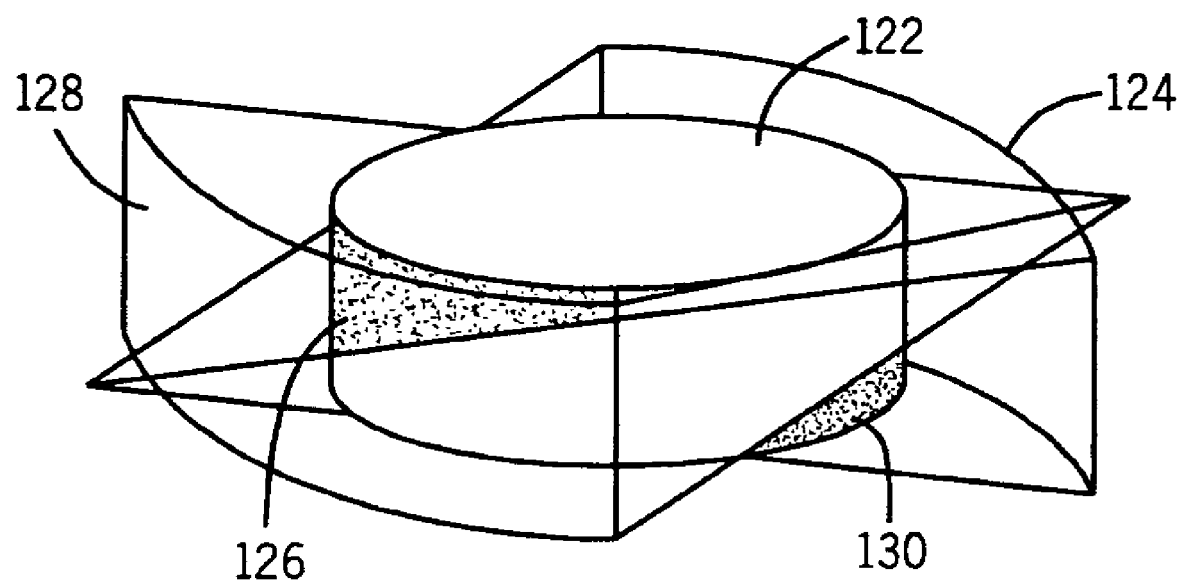
FIG. 11 is a schematic illustrating an imaging volume being imaged in a pair of complimentary half-scans.

For a step-and-shoot acquisition, such as that described herein, the completely sampled region is less than a cylindrical disc with its height equal to the detector isocenter coverage. That is, the cone beam geometry reduces the coverage of each projection to a region with data acquisition areas much narrower than the desired volume near the source, as illustrated in FIG. 11. The volume 122, from which data is acquired, is not completely sampled in a single half-scan. In this regard, the fan beam 124 of a first half-scan fails to acquire data from region 126 of the sampling volume 122. As a result, image artifacts can become prevalent over the $2\pi$ angular range.

To reduce the occurrence of image artifacts in a step-and-shoot cardiac gated CT acquisition, the present invention is further directed to controlling gantry rotation during data acquisition such that the difference between the projection angles of a pair of complimentary half-scan is approximately $\pi$ radians. That is, because of the cone beam geometry of an x-ray fan beam, the region closer to the detector covers a z-extent that is significantly higher than the coverage at detector isocenter. Therefore, two projections that are spaced one detector width (at isocenter) apart, and their projection angles differ by $\pi$ radians, there is little sampling gap in the sampling volume. The two projections, therefore, form a complimentary pair. This is illustrated in FIG. 11.

As shown, the projections defined by fan beam 128 forms a complimentary pair with the projections of fan beam 124. Moreover, fan beam 128 captures data from the unsampled region 126 of fan beam 124 and results in an unsampled region 130 that is sampled by the fan beam 124. For cardiac gated CT imaging, it is desired to maintain a desired relationship between fan beams 124 and 128. This relationship is maintained by controlling the speed at which the gantry rotates, and as a result, the x-ray source, rotates. Moreover, gantry rotation must be controlled such that CT data acquisition is synchronized with cardiac motion of the subject. This is achieved by acquiring cardiac motion data before data acquisition using an ECG monitor. By measuring ECG data prior to data acquisition, the heart rate of the subject can be ascertained before data acquisition of CT data. In this regard, the gantry controller or other controller may set gantry rotation at a speed that ensures that the center angles of two neighboring half-scans differ within a range of $\pi$ radians. Specifically, the gantry controller sets a gantry rotational speed based on the following expression:

$$\pi - \Gamma \leq \beta_A - \beta_B \leq \pi + \Gamma \qquad \text{Eqn. (4)}$$

where $\Gamma$ is a parameter that describes the allowable variation from $\pi$, $\beta_A$ and $\beta_B$ are the center projection angles of neighboring half-scans. While a number of values for $\Gamma$ may be used, in one preferred embodiment, a value of $\pi/4$ is used. It is preferred that $\Gamma$ be selected to have a value that satisfies a balance between image quality and robustness for heart rate variation. While it is contemplated that values for $\Gamma$ greater than $\pi/4$ may be used, it is preferred that a $\Gamma$ value of $\pi/4$ or less be used. In this regard, the center projection angles between neighboring half-scans differ by roughly $\pi$ radians.

The present invention has been described with respect to segmenting full gantry rotations into a pair of half-scans; however, one skilled in the art will appreciate that a full gantry rotation may be segmented into multiple partial scans. In this regard, gantry rotation is controlled such that a desired relationship between the center projection angles of neighboring partial scans is maintained to reduce image artifacts.

Figure 12:
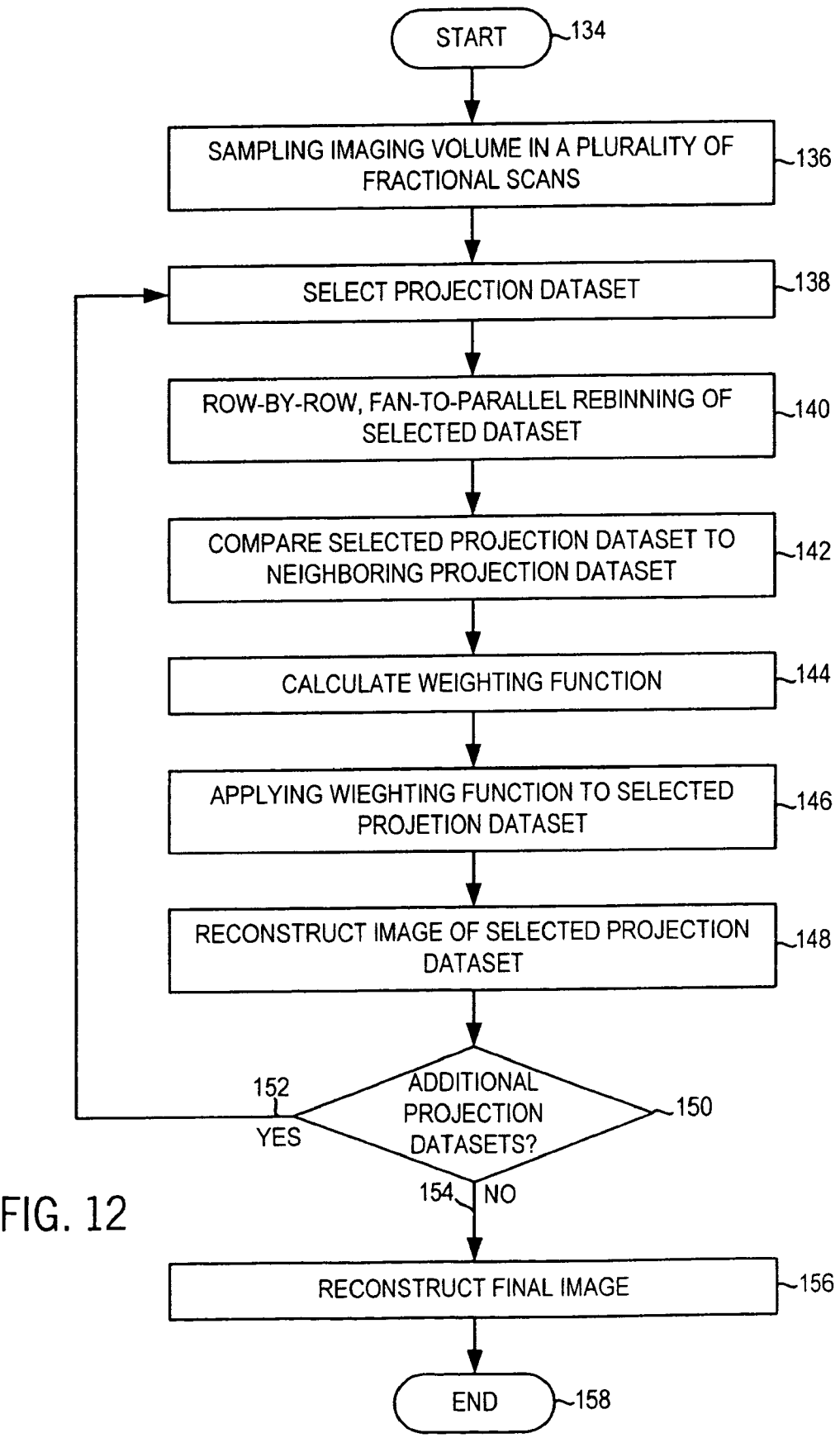
FIG. 12 is a flow chart setting forth the steps of a partial-scan technique in accordance with the present invention.

Referring now to FIG. 12, a method setting forth steps of a data acquisition and image reconstruction technique particularly applicable to partial-scans is illustrated. As will be described, this reconstruction process combines the contributions of neighboring partial-scans, i.e. half-scans, to compensate for missed or unsampled regions in a single partial-scan. For purposes of illustration, this reconstruction technique will be described to half-scans, but it is understood that the technique may be extended to other types of partial-scans.

The imaging technique 132 begins at 134 with the sampling of an imaging volume in a plurality of fractional or partial-scans 136. As described above, it is preferred that the center angles of neighboring half-scans differ within a range defined by $(\pi-\Gamma, \pi+\Gamma)$. After several projection datasets have been acquired from the sampling volume, then each projection dataset undergoes a weighting and rebinning process, as described below.

Technique 132 continues with the selection of a projection dataset 138 for processing. The selected projection dataset undergoes a row-by-row, fan-to-parallel beam rebinning 140. In this regard, for the projection dataset, $p_A(S, v, \beta)$, a neighboring projection sample, $p_B(s', v', \beta')$, where $|\beta'-\beta|=n\pi$ with n being an odd integer, is examined 142. From the comparison of the neighboring datasets, a weighting function is determined 144. Specifically, by comparing v and v', a weighting function, $\xi_A(x, y, z)$, is defined during the backprojection step of the reconstruction, as defined in the following expression:

$$\xi_A(x, y, z) = \frac{\varepsilon_A(x, y, z)}{\varepsilon_A(x, y, z) + \varepsilon_B(x, y, z)}, \qquad \text{(Eqn. 5)}$$

where:

$$\varepsilon_A(x, y, z) = \begin{cases} 0, & |v| > v_m + \Delta \\ 1 - |v - v_m|/\Delta, & v_m \leq v < v_m + \Delta. \\ 1, & |v| < v_m \end{cases} \qquad \text{(Eqn. 6)}$$

$\varepsilon_B$ is defined in a similar fashion. The weighting function is then applied to the selected dataset 146 and an image of the selected projection dataset is reconstructed 148 in accordance with the following reconstruction equation:

$$f_A(x, y, z) = \frac{1}{2} \int_0^{\pi+2\gamma_m} \left(\frac{D}{D+y'}\right)^2 \xi_A(x, y, z) d\beta \times \qquad \text{Eqn. (7)}$$

$$\int_{-\infty}^{\infty} \frac{D}{\sqrt{D^2 + s^2 + v^2}} w(s, \beta) q(s, v, \beta) h(s' - s) ds.$$

The technique then proceeds to step 150 to determine if there are any additional projection datasets to be processed. If so 150, 152, steps 138-148 are repeated for each projection dataset. Once all projection datasets have been processed 150, 154, a final image is reconstructed 156 from the summation of neighboring reconstructions. The reconstruction process then ends at 158.

While the aforementioned steps have been described with respect to the processing of raw projection data, it is contemplated that the aforementioned steps can be equivalently carried out in image space. That is, a quality factor, $\eta(x, y, z)$, is defined for each reconstructed pixel of a single half-scan dataset. The quality factor can be defined as:

$$\eta(x, y, z) = \int_0^{\pi+\gamma_m} \varphi(v, \beta) d\beta, \qquad \text{(Eqn. 8)}$$

where:

$$\varphi(v, \beta) = \begin{cases} 0, & |v| \le v_m \\ |v - v_m|/\Delta, & v_m < v < v_m + \Delta \\ 1, & |v| \ge v_m + \Delta \end{cases} \qquad \text{(Eqn. 9)}$$

It is noted that for the center regions where sampling is complete, i.e. no undersampling, $\eta=0$. For regions that experienced significant undersampling, $\eta$ is large. The final reconstructed image is then the combination of two adjacent half-scan images as defined by the following expression:

$$f(x, y, z) = \frac{\eta_B(x, y, z)}{\eta_A(x, y, z) + \eta_B(x, y, z)} f_A(x, y, z) + \qquad \text{(Eqn. 10)}$$

$$\frac{\eta_A(x, y, z)}{\eta_A(x, y, z) + \eta_B(x, y, z)} f_B(x, y, z).$$

The present invention has been described with respect to no overlapping of scan between adjacent step-and-shoot scans. Alternately, it is contemplated that the half-scans can be defined to provide for overlapping to enhance image quality. In this regard, it is contemplated that additional data blending may be carried out in the overlapped regions during image reconstruction.

Also, it is recognized that the present invention may be applicable to sector-based scanning in addition to half-scans or other partial-scans. In this regard, subject position remains fixed for several cardiac cycles. Within each cycle, a fraction of a required projection dataset is acquired. When the scan speed is selected to be asynchronized with the heart rate, non-redundant projections can be acquired over multiple cardiac cycles.

During the reconstruction process, the acquired datasets are blended together to form a complete dataset. This approach enables improved temporal resolution. Alternatively, the table can index at a fraction of the detector coverage over each cardiac cycle. The fraction is determined by the number of sectors required for the reconstruction. For example, when using a two-sector acquisition, the table is moved roughly fifty percent of the scanner coverage in each cardiac cycle.

It should be understood that the above described acquisition can be easily extended to the acquisition mode in which multiple phases of the heart need to be scanned. In such protocol, the x-ray will be on until the projection data for all cardiac phases are acquired before the table is indexed to the next location. For example, it is possible to scan a patient in end-diastole and end-systole phases. During the data acquisition, the datasets corresponding to these two phases are acquired before the table is moved to the next location.

Therefore, the present invention includes a CT imaging system having a rotatable gantry with an opening therein to receive a subject to be scanned as well as a table movable fore and aft through the opening. The system also has a controller that is configured to move a subject disposed on the table to a first data acquisition position. The controller is further configured to coordinate acquisition of imaging data from the subject at the first data acquisition position with a cardiac cycle of the subject. Moreover, the controller is configured to advance the subject to a subject data acquisition position different from the first data acquisition position only if the imaging data acquired at the first data acquisition position is deemed acceptable.

The present invention further includes a method of cardiac CT imaging whereby a subject is positioned at a first data acquisition position of a number of discrete data acquisition positions. A dataset of gated CT data is then acquired from a cardiac region of the subject with the subject positioned at the first data acquisition position. The method further includes determining if the dataset is valid and, if so, positioning a subject at a second data acquisition position different from the first data acquisition position. If the dataset is invalid, the method further includes reacquiring the dataset of gated CT data from the cardiac region of the subject with the subject positioned at the first data acquisition position.

The invention is also embodied in a computer readable storage medium having a computer program stored thereon and representing a set of instructions is disclosed. The set of instructions, when executed by a computer, causes the computer to incrementally translate a scan subject positioned on a table of a CT system through a number of discrete scan positions. The computer is further caused to acquire physiologically gated CT data at each scan position and monitor physiological motion activity of the scan subject during data acquisition at each scan position. The set of instructions further causes the computer to suspend data acquisition from the scan subject at a scan position if an irregularity in physiological motion activity of the scan subject is detected during data acquisition from the scan subject when positioned at the scan position.

The present invention is further directed to a scanner comprising a gantry having an x-ray source disposed therein and configured to rotate about an opening having a subject to be scanned disposed therein. The scanner further has an ECG monitor configured to acquire cardiac motion data from the subject to be scanned and a controller configured to define a full gantry rotation into a number of partial scans. The controller is further configured to rotate the gantry such that center projection angles of neighboring partial-scans differ by roughly $\pi$ radians.

A CT imaging system is also disclosed as having a rotatable gantry including an opening therein to receive a subject to be scanned and an x-ray source disposed within the rotatable gantry and configured to project a fan beam of x-rays at the subject during CT data acquisition. The system further has a table movable fore and aft through the opening and a computer programmed to acquire cardiac gated CT data from a sampling region in a pair of complimentary half-scans. The computer is further programmed to cause rotation of the rotatable gantry at a gantry speed during CT data acquisition form the sampling region such that a center projection angle of x-rays in one half-scan differs from the center projection angle of x-rays in a complimentary half-scan by approximately π radians.

A method of CT imaging is also disclosed. The method includes defining a number of discrete scan positions through which a scan subject is to be translated for data acquisition and rotating an x-ray source through a series of projection angles and at a rotational speed about the scan subject along an annular path of rotation when the scan subject is positioned at a discrete scan position. The method further includes defining each full rotation of the x-ray source into a first half-scan and a second half-scan and, for each projection angle of the first half-scan, defining a complimentary projection angle of the second half-scan. The method also includes controlling the rotational speed of the x-ray source such that the projection angles of the first half-scan differ from their complimentary projection angles of the second half-scan by approximately π radians.

A CT scanner is disclosed and includes an x-ray source configured to project x-rays at a subject to be scanned and an x-ray detector assembly configured to detect x-rays projected by the x-ray source and attenuated by the subject. The CT scanner also includes a computer programmed to define an imaging volume to be imaged in a pair of neighboring partial-scans and cause acquisition of a first set of CT data from less than all the imaging volume in a first partial-scan. The computer is further programmed to cause acquisition of a second set of CT data from less than all the imaging volume in a second partial-scan and combine the first and the second sets of CT data into a composite dataset having a spatial coverage of the imaging volume. The computer then reconstructs a CT image of the imaging volume from the composite dataset.

A method of CT imaging is also disclosed and includes the steps of defining an imaging volume from which CT data is to be acquired and translating a subject to be scanned to one of a number of discrete scan positions. The method further includes repeatedly acquiring CT data from the imaging volume in a series of fractional scans while the subject is positioned at the one discrete scan position and blending the CT data acquired with the series of fractional scans into a single dataset for reconstruction.

The invention also includes a computer readable storage medium having a computer program stored thereon and representing a set of instructions that when executed by a computer causes the computer to acquire a first set of cardiac gated CT data in a first half-scan and acquire a second set of cardiac gated CT data in a second half-scan that captures the second set of cardiac gated CT data from a portion of a sampling region that neighbors another portion of the sampling region from which the first set of cardiac gated CT data is acquired. The computer is further caused to compare the first set of cardiac gated CT data to the second set of cardiac gated CT data to determine a weighting function and weight the first set of cardiac gated CT data by the weighting function. The computer then combines the weighted first set of cardiac gated CT data with the second set of cardiac gated CT data for image reconstruction of the sampling region.

The present invention has been described in terms of the preferred embodiment, and it is recognized that equivalents, alternatives, and modifications, aside from those expressly stated, are possible and within the scope of the appending claims.

What is claimed is:

1. A CT scanner comprising:
    an x-ray source mounted on a rotatable gantry and configured to project x-rays at a subject to be scanned and an x-ray detector assembly configured to detect x-rays projected by the x-ray source and attenuated by the subject; and
    a computer programmed to:
        define an imaging volume to be imaged in a pair of neighboring partial-scans;
        cause acquisition of a first set of CT data from a portion of the imaging volume in a first partial-scan;
        cause acquisition of a second set of CT data from another portion of the imaging volume in a second partial-scan;
        control a rotational speed of the gantry based on a measured cardiac motion such that the acquisition of the first and second sets of CT data are synchronized with the measured cardiac motion and such that center angles of the first and second partial-scans differ by approximately π radians;
        combine the first and the second sets of CT data into a composite dataset having a spatial coverage of the imaging volume; and
        reconstruct a CT image of the imaging volume from the composite dataset.

2. The CT scanner of claim 1 wherein the computer is further programmed to define a spatial coverage for the first partial-scan that partially overlaps a spatial coverage of the second partial-scan.

3. The CT scanner of claim 1 wherein the computer is further programmed to control the rotational speed of the gantry such that center projection angles of the first and second partial-scans differ within a specified range from 7t in accordance with the following expression:

$$\pi-\Gamma \leq \beta_A-\beta_B \leq \pi+\Gamma,$$

where $\Gamma$ is a parameter that describes the allowable variation from $\pi$, and $\beta_A$ and $\beta_B$ are the center projection angles of neighboring half-scans.

4. The CT scanner of claim 3 where $\Gamma$ has a value of $\pi/4$.

5. The CT scanner of claim 1 wherein the computer is further programmed to perform a row-by-row, fan-to-parallel beam rebinning of the first and the second sets of CT data.

6. The CT scanner of claim 5 wherein the computer is further programmed to one of weight the first set of CT data based on the second set of CT data and weight the second set of CT data based on the first set of CT data.

7. The CT scanner of claim 1 further comprising an ECG monitor that monitors the cardiac motion of the subject.

8. The CT scanner of claim 1 wherein the computer is further programmed to cause acquisition of the first and the second sets of CT data while the subject is fixed at a given table position.

9. The CT scanner of claim 1 wherein the computer is further programmed to define the neighboring partial scans as half-scans.

10. The CT scanner of claim 1 wherein the computer is further programmed to cause translation of the subject through an opening in the gantry a fraction of detector coverage over each cardiac cycle measured of the subject.

11. A method of CT imaging, the method comprising:
    defining an imaging volume from which CT data is to be acquired;

translating a subject to be scanned to one of a number of discrete scan positions;

repeatedly acquiring CT data from the imaging volume in a series of fractional scans while the subject is positioned at the one discrete scan position;

maintaining the series of fractional scans in a desired relationship by controlling the rotational speed of a CT gantry such that center angles of neighboring fractional scans differ by approximately π radians; and blending the CT data acquired with the series of fractional scans into a single dataset for reconstruction.

12. The method of claim 11 further comprising synchronizing CT acquisition with cardiac activity of the subject.

13. The method of claim 12 further comprising acquiring the CT data during a series of cardiac cycles with the subject fixed at the one discrete scan position.

14. The method of claim 12 further comprising including translating the subject at a fraction of detector coverage in each cardiac cycle.

15. The method of claim 12 further comprising acquiring the CT data from all cardiac phases of a cardiac cycle before translating the subject to a next discrete scan position.

16. The method of claim 11 wherein each fractional scan is a half scan.

17. The method of claim 16 wherein spatial coverage of one half scan partially overlaps that of a neighboring half scan.

18. The method of claim 11 further comprising determining if CT data acquired with the subject at the one discrete scan position is valid and if so, translating the subject to a next discrete scan position; otherwise, re-acquiring CT data from the subject with the subject at the one discrete scan position.

19. A computer readable storage medium having a computer program stored thereon and representing a set of instructions that when executed by a computer causes the computer to:

acquire a first set of cardiac gated CT data in a first half-scan;

acquire a second set of cardiac gated CT data in a second half-scan that captures the second set of cardiac gated CT data from a portion of a sampling region that neighbors another portion of the sampling region from which the first set of cardiac gated CT data is acquired;

control rotational speed of a CT gantry such that, for acquisition of the first and second sets of CT data, a center projection angle of the second half-scan differs from a center projection angle of the first half-scan within a specified range from π;

compare the first set of cardiac gated CT data to the second set of cardiac gated CT data to determine a weighting function;

weight the first set of cardiac gated CT data by the weighting function; and combine the weighted first set of cardiac gated CT data with the second set of cardiac gated CT data for image reconstruction of the sampling region.

20. The computer readable storage medium of claim 19 wherein the computer is further caused to determine the weighting function for the first set of cardiac gated CT data from the following expression:

$$\xi_A(x, y, z) = \frac{\varepsilon_A(x, y, z)}{\varepsilon_A(x, y, z) + \varepsilon_B(x, y, z)};$$

where $$\varepsilon_A(x, y, z) = \begin{cases} 0, & |v| > v_m + \Delta \\ 1 - |v - v_m|/\Delta, & v_m \le v < v_m + \Delta \\ 1, & |v| < v_m \end{cases}$$

and $\epsilon_B$ is similarly defined and wherein $v$ and $v_m$ are neighboring projection samples in the first half-scan.

21. The computer readable storage medium of claim 20 wherein the computer is further caused to reconstruct an image for the weighted first set of cardiac gated CT data in accordance with the following expression:

$$f_A(x, y, z) = \frac{1}{2}\int_0^{\pi+2\gamma_m} \left(\frac{D}{D+y'}\right)^2 \xi_A(x, y, z) d\beta \times$$
$$\int_{-\infty}^{\infty} \frac{D}{\sqrt{D^2 + s^2 + v^2}}$$
$$w(s, \beta)q(s, v, \beta)h(s' - s)ds,$$

where D is x-ray source to system isocenter distance, s and v are projection channel and row locations according to reconstructed pixel (x,y,z), β is the projection angle, γ is the detector fan angle corresponding to s, and w(s, β) is the half-scan weight.

22. The computer readable storage medium of claim 20 wherein the computer is further programmed to transform the first and the second sets of cardiac gated CT data to image space before comparing the first and the second sets of cardiac gated CT data.

23. The computer readable storage medium of claim 22 wherein the weighting function includes a quality factor defined as:

$$\eta(x, y, z) = \int_0^{\pi+\gamma_m} \varphi(v, \beta) d\beta,$$

where $$\varphi(v, \beta) = \begin{cases} 0, & |v| \le v_m \\ |v - v_m|/\Delta, & v_m < v < v_m + \Delta, \\ 1, & |v| \ge v_m + \Delta \end{cases}$$

and wherein $v$ and $v_m$ are neighboring projection samples.

24. The computer readable storage medium of claim 23 wherein the computer is further caused to reconstruct an image of the sampling region from two adjacent half-scan images defined by:

$$f(x, y, z) = \frac{\eta_B(x, y, z)}{\eta_A(x, y, z) + \eta_B(x, y, z)} f_A(x, y, z) + \frac{\eta_A(x, y, z)}{\eta_A(x, y, z) + \eta_B(x, y, z)} f_B(x, y, z),$$

where $n_A(x,y,z)$ and $n_B(x,y,z)$ are the quality factor for the first and second half-scans.

* * * * *

UNITED STATES PATENT AND TRADEMARK OFFICE
CERTIFICATE OF CORRECTION

PATENT NO. : 7,570,733 B2  
APPLICATION NO. : 11/149993  
DATED : August 4, 2009  
INVENTOR(S) : Hsieh et al.

Page 1 of 1

It is certified that error appears in the above-identified patent and that said Letters Patent is hereby corrected as shown below:

Col. 14, line 37 (Claim 3), delete "7t" and substitute therefore -- $\pi$ --;

Col. 15, line 29 (Claim 17), delete "half scan partially overlaps that of a neighboring half scan." and substitute therefore -- half-scan partially overlaps that of a neighboring half-scan. --;

Col. 16, line 11 (Claim 20), delete "$\epsilon_B$" and substitute therefore -- $\varepsilon_B$ --.

Signed and Sealed this

Twentieth Day of October, 2009

David J. Kappos  
*Director of the United States Patent and Trademark Office*